United States Patent [19]

Hoch et al.

[11] 4,067,903
[45] Jan. 10, 1978

[54] MANUFACTURE OF ARYLAMINES

[75] Inventors: Helmut Hoch, Wachenheim; Horst Scheuermann, Ludwigshafen, both of Germany

[73] Assignee: BASF Aktiengesellschaft, Ludwigshafen, Germany

[21] Appl. No.: 725,395

[22] Filed: Sept. 22, 1976

[30] Foreign Application Priority Data

Oct. 4, 1975 Germany ............................. 2544504
Nov. 4, 1975 Germany ............................. 2549305
Nov. 7, 1975 Germany ............................. 2549957
Feb. 18, 1976 Germany ............................. 2606363

[51] Int. Cl.$^2$ .................... C07C 93/02; C07C 93/06; C07C 87/28; C07C 87/60
[52] U.S. Cl. ............................ 260/570.6; 252/431 P; 260/570.7; 260/570.8 R; 260/570.9; 260/576; 260/577
[58] Field of Search .................... 252/431 P; 260/576, 260/571, 570.9, 570.8 R, 570.5 CA, 570.6, 570.7

[56] References Cited

U.S. PATENT DOCUMENTS 2,503,778   4/1950   Stone et al. .......................... 260/576

FOREIGN PATENT DOCUMENTS 1,958,168   7/1970   Germany ............................. 260/576
48-91194   11/1973   Japan .................................. 260/576

OTHER PUBLICATIONS

Vrany et al., "Chemical Abstracts," vol. 69, Abstract No. 97450g (1968).

Primary Examiner—Daniel E. Wyman
Assistant Examiner—John J. Doll
Attorney, Agent, or Firm—Keil, Thompson & Shurtleff

[57] ABSTRACT

Arylamines are manufactured by reacting alcohols with amines in the presence of phosphorus-III compounds. The arylamines I manufactured by the process of the invention are intermediates for the manufacture of crop protection agents, optical brighteners, especially aminocoumarin derivatives, and dyes, especially of the xanthene, pyronine, rhodamine, oxazine, azo, triphenylmethane and diphenylmethane series.

12 Claims, No Drawings

MANUFACTURE OF ARYLAMINES

The present invention relates to a new process for the manufacture of arylamines by reacting alcohols with amines in the presence of phosphorus-III compounds.

Houben-Weyl, Methoden der Organischen Chemie, volume 111, pages 160 – 170, discloses that phenols can be reacted with aliphatic amines to give the corresponding aniline compounds. As is stated in more detail on page 162, the direct reaction is rarely carried out, even in the case of relatively reactive phenols; as a rule, the reaction is instead carried out in the presence of added dehydrating agents or catalysts, e.g. hydrochlorides of the amines to be reacted, sulfates, phosphates, chlorides, boric acid or iodine. The yield and purity of the end products of this process are unsatisfactory; thus, reaction of resorcinol with various amines in the presence of phosphoric acid gives yields of only from 7 to 16% or, in the case of a greater excess of amine, 23% (Journal of Medicinal Chemistry, 13 (1970), 371 and 375). In particular, tarry and resinous materials separate out; a further disadvantage is that substituted m-phenylenediamines are formed. Under certain reaction conditions, e.g. if the reaction time is long, the reaction temperature is high and/or acids or salts are present as catalysts, the formation of these N-substituted m-phenylenediamines is the main reaction. British Pat. No. 168,689 discloses that, for example in the presence of the sulfite or hydrochloride of the amine to be reacted, both hydroxyl groups of resorcinol react and the amount of substituted m-aminophenol obtained is insignificant.

German Pat. No. 14,612 discloses that $\beta$-naphthol can be reacted with an excess of primary and secondary amines, in the form of their hydrochlorides, for from 7 to 12 hours at from 170° to 210° C, under pressure, to give naphthylamines. The yields are unsatisfactory, particularly on an industrial scale. The patent further discloses that there is a danger of tertiary bases being formed because of a secondary reaction, at higher temperature, of the secondary amine formed with unreacted naphthol. This causes a deterioration of the yield and purity of the end product. In this context, it has also been disclosed that at higher temperatures dealkylation and transalkylation reactions of the alkylamines employed, to give more highly and less highly alkylated amines, take place. Thus, German Laid-open Application No. 2,301,203 discloses that in the case of all the known processes, including the amination of naphthol, naphthylamines are present in the end product; it is therefore necessary to purify the alkylnaphthylamines produced. Houben-Weyl, loc. cit., page 135 further discloses that N-n-butylaniline rearranges to 4-n-butylaniline at a temperature as low as 240° C.

Berichte der Deutschen Chemischen Gesellschaft, 14 (1881), 2,343 discloses that the reaction of $\beta$-naphthol with excess ammonium acetate, with or without added glacial acetic acid, at 270° – 280° C gives $\beta$-acetaminonaphthalene and, as by-products formed in minor amounts, the free amine as well as $\beta$-dinaphthylamine. Houben-Weyl (loc. cit., pages 162 and 164) recommends the use of dehydrating salts for the reaction of naphthols and shows that in the reaction with ammonia dinaphthylamine is also formed in significant amounts; the naphthylamine produced can also be converted, under appropriate conditions, into dinaphthylamine and ammonia (page 165). 1- and 2-naphthol, with ammonia and calcium chloride as the catalyst, give 1- and 2-naphthylamine, with 1,1'- and 2,2'-dinaphthylamine as the respective by-products, whilst when using zinc chloride these by-products are obtained as the main product.

German Pat. No. 848,196 discloses that the manufacture of secondary aromatic amines by reacting primary aromatic amines with phenols in the presence of iodine as the catalyst requires a very long reaction time. It is true that if the iodine is replaced by zinc chloride or sulfuric acid, the reaction time can be reduced, but solid, infusible residues are formed, which have poor heat conductivity, diminish the yield and worsen heat transfer to a point that it is no longer possible to continue the condensation. According to the disclosure of this patent, organic sulfonic acids, especially aromatic sulfonic acids, are added as catalysts for the condensation of phenols with primary aromatic amines. The residues formed in this reaction are fluid when hot. In the case of naphthols, this reaction gives good yields of end product only in the case of $\beta$-naphthol. According to the disclosure in Houben-Weyl (loc. cit., page 165), the differing reactivities of $\alpha$- and $\beta$-naphthol in respect of reaction with arylamines also manifest themselves in the presence of iodine, calcium chloride or a sulfonic acid as the catalyst.

U.S. Pat. No. 2,503,778 discloses that when trialkyl phosphates are used as catalysts for the reaction of hydroquinone with aniline, yields of N,N'-diphenyl-p-phenylenediamine of from 73 to 80.5% are obtained, as is shown by all the examples. Reactions of resorcinol, hydroquinone or other phenols with ammonia or amines in the presence of ammonium phosphates or ammonium arsenates for a reaction time of more than 12 hours give yields of from 22 to 80%, according to the experiments described in U.S. Pat. No. 2,376,112.

The reaction of aliphatic alcohols with amines in the presence of acids or alkalis to give corresponding alkylamines is also disclosed in Houben-Weyl (loc. cit., pages 134 – 136). According to this disclosure, amine mixtures are to be expected as the product of the reaction. The reaction also depends on the ratio in which the reactants are mixed, on the reaction conditions and, in the case of aromatic amines, on their structure. Aromatic amines can be alkylated in the nucleus; the temperature of rearrangement of the alkyl group, from the nitrogen atom to the nucleus of the aromatic amine, depends on the nature of the alcohol. The reaction of primary alcohols with aniline, 4-nitroaniline, 4-aminophenol or 2-naphthylamine may go as far as the tertiary amine. It is pointed out (on page 135) that an excess of primary alcohol results in a peralkylation, to give the quaternary ammonium salts, if copious amounts of acid are employed to accelerate the reaction.

The reaction of alcohols with aromatic amines in the presence of their hydrochlorides or sulfates, or in the presence of hydrogen iodide, ammonium iodide, boron fluoride, methyl iodide, ammonium zinc chloride and alkylphenylammonium iodide also fails to give only a single product, so that secondary and tertiary amines must be separated off by separate processes.

It is an object of the present invention to provide a new process whereby arylamines can be manufactured more simply and more economically, with improved yield, improved space-time yield and greater purity.

We have found that this object is achieved and that arylamines of the formula $$\begin{array}{c} R^5 \\ | \\ R^1\!-\!N\!-\!R^2 \end{array} \qquad \text{I}$$

where $R^1$ is

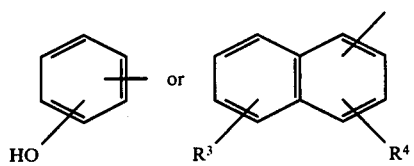

or is an aliphatic, cycloaliphatic or araliphatic radical, $R^2$ is an aromatic radical and, if $R^1$ is

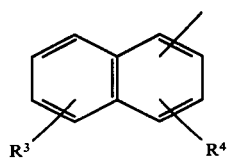

may also be an aliphatic, cycloaliphatic or araliphatic radical, $R^3$ and $R^4$ may be identical or different and each is hydrogen, an aliphatic radical or alkoxy and $R^5$ is hydrogen or, if $R^1$ is an aliphatic, cycloaliphatic or araliphatic radical, may also be an aliphatic, cycloaliphatic or araliphatic radical, are obtained advantageously when amines of the formula $$\begin{array}{c} H \\ | \\ R^2\!-\!N\!-\!R^5 \end{array} \qquad \text{II}$$

where $R^2$ and $R^5$ have the above meanings, are reacted with alcohols of the formula $$R^1 - OH \qquad \text{III}$$

where $R^1$ has the above meanings, in the presence of a phosphorus-III compound of the formula $$\begin{array}{c} R^6O\!-\!P\!-\!OR^6 \\ | \\ OR^6 \end{array} \qquad \text{IV}$$

where the individual $R^6$ radicals may be identical or different and each is hydrogen or an aliphatic, araliphatic or aromatic radical, as the catalyst.

Further, we have found that arylamines I are obtained advantageously when primary, aromatic amines of the formula $$\begin{array}{c} H \\ | \\ R^2\!-\!N\!-\!H \end{array} \qquad \text{II}$$

where $R^2$ is an aromatic radical, are reacted with phenols of the formula $$R^1 - OH \qquad \text{III}$$

where $R^1$ is

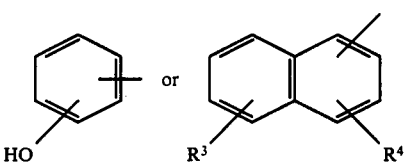

and $R^3$ and $R^4$ may be identical or different and each is hydrogen, an aliphatic radical or alkoxy, in the presence of a triaryl phosphite of the formula $$\begin{array}{c} R^6O\!-\!P\!-\!OR^6 \\ | \\ OR^6 \end{array} \qquad \text{IV}$$

where the individual $R^6$ radicals may be identical or different and each is an aromatic radical, as the catalyst.

Further, we have found that arylamines I are obtained advantageously when primary, aromatic amines of the formula $$\begin{array}{c} H \\ | \\ R^2\!-\!N\!-\!H \end{array} \qquad \text{II}$$

where $R^2$ is an aromatic radical, are reacted with phenols of the formula $$R^1 - OH \qquad \text{III}$$

where $R^1$ is

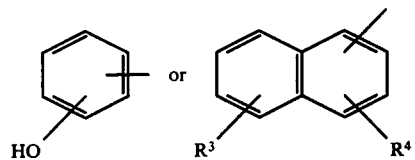

and $R^3$ and $R^4$ may be identical or different and each is hydrogen, an aliphatic radical or alkoxy, in the presence of a phosphorus-III compound of the formula $$\begin{array}{c} R^6O\!-\!P\!-\!OR^6 \\ | \\ OR^6 \end{array} \qquad \text{IV}$$

where the individual $R^6$ radicals may be identical or different and each is hydrogen or an aliphatic or araliphatic radical, and one or 2 $R^6$ radicals may also each be an aromatic radical, as the catalyst.

Further, we have found that arylamines I are obtained advantageously when primary amines of the formula $$\begin{array}{c} H \\ | \\ R^2\!-\!N\!-\!H \end{array} \qquad \text{II}$$

where $R^2$ is an aliphatic, cycloaliphatic or araliphatic radical, are reacted with naphthols of the formula

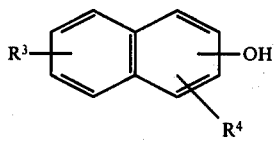

where $R^3$ and $R^4$ may be identical or different and each is hydrogen or an aliphatic radical or alkoxy, in the presence of a phosphorus-III compound of the formula

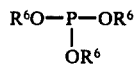  IV where the individual $R^6$ radicals may be identical or different and each is hydrogen or an aliphatic, araliphatic or aromatic radical, as the catalyst.

Further, we have found that arylamines I are obtained advantageously when aromatic amines of the formula

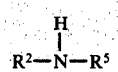  II where $R^5$ is an aliphatic, cycloaliphatic or araliphatic radical or hydrogen and $R^2$ is an aromatic radical, are reacted with alcohols of the formula

  III where $R^1$ is an aliphatic, cycloaliphatic or araliphatic radical, in the presence of a phosphorus-III compound of the formula

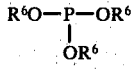  IV where the individual $R^6$ radicals may be identical or different and each is hydrogen or an aliphatic, araliphatic or aromatic radical, as the catalyst.

When resorcinol or α-naphthol and aniline are used, the reaction may be represented by the following equations:

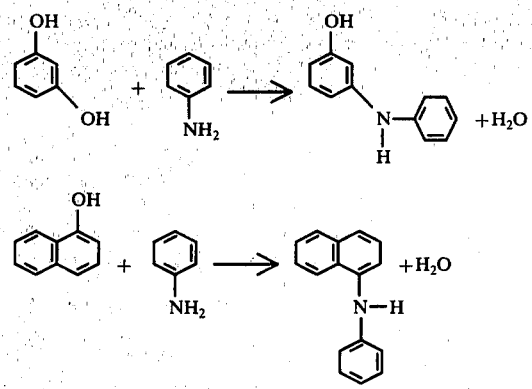

Where ethylamine and α-naphthol are used, the reaction can be represented by the following equation:

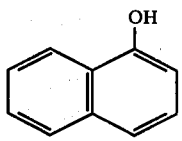 + $CH_3-CH_2-NH_2$ ⟶

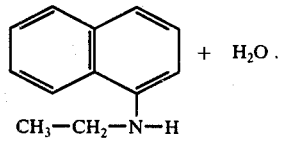 + $H_2O$.

Where m-toluidine and 2-phenylethanol are used, the reaction can be represented by the following equation:

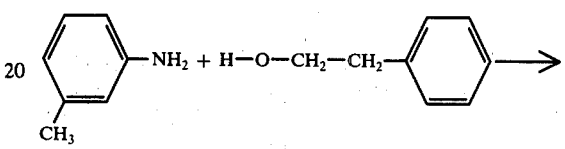

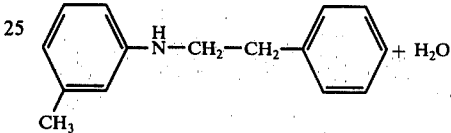 + $H_2O$

Compared to conventional processes, the process of the invention gives arylamines more simply and more economically, in better yield, with better space-time yield, and in higher purity. Surprisingly, no significant formation of tarry residues or residues which inhibit heat transfer, or of N,N'-disubstituted m-phenylenediamines, is observed; expensive purification operations are avoided and in many cases the crude end product can be used directly for subsequent syntheses. From the point of view of the use of corrosive strong acids and acid salts as catalysts, the process of the invention is safer to operate and causes less environmental pollution; the plant and pipelines suffer far less corrosion. Accordingly, it is possible to dispense with lead, enamel, nickel alloys or other highly corrosion-resistant and heat-resistant linings.

Compared to the conventional processes, especially those which do not use a catalyst, the present process avoids very high reaction temperatures and reaction pressures, which favor resinification of the reaction mixture, and thus avoids lengthy heating and cooling operations. The amine can be used economically and it is even possible to employ approximately stoichiometric amounts. Compared to conventional processes using relatively high reaction temperatures of at least 250° C, e.g. the process described in German Pat. No. 848,196, the present process gives higher yields of end product in spite of the lower temperatures used. Compared to syntheses of N-alkylnaphthylamines which are prepared by N-alkylation of α- or β-naphthylamine, and with reference to the high toxicity of β-naphthylamine, the process of the invention, particularly on an industrial scale, provides safer operation and less pollution of the environment, and is also safer with respect to the health of the operatives. Compared to syntheses of N-alkylarylamines which are carried out by N-alkylation of primary aromatic amines, the process of the invention is more selective and no significant formation of heterogeneous mixtures is observed. All these advantageous results obtained with the process of the invention are surprising. From the prior art, a lower rate of reaction and substantially poorer yield would have been expected particularly in the case of α-naphthols and phosphorus derivatives as the catalyst. It would also have been expected that, at the very least, substantially higher temperatures, e.g. of from 250° to 300° C, and reaction times of at least 12 hours, would be necessary to achieve satisfactory results. Surprisingly, no significant amounts of acylated by-products, tertiary amine bases and naphthylamines, which could result from the reaction of the naphthols with the decomposition products of the amines employed, or of nuclear-alkylated amines, formed by rearrangement, are produced.

The starting materials are reacted in the stoichiometric ratio or non-stoichiometric ratio, preferably, in the case of aromatic alcohols III, in a ratio of from 1 to 3.5, advantageously from 1 to 1.8 and especially from 1 to 1.3, moles of starting material II per mole of starting material III, and in the case of aliphatic, cycloaliphatic or araliphatic alcohols III preferably in a ratio of from 0.3 to 4, advantageously from 0.5 to 2, moles of starting material II per mole of alcohol III. In the case of aliphatic, cycloaliphatic or araliphatic alcohols III, and of the reaction of primary amines, it is advantageous to use from 1 to 4 moles of starting material II per mole of alcohol III to produce secondary amines and from 0.3 to 0.7 mole of starting material II per mole of alcohol III to produce tertiary amines. Preferred starting materials II and III and, accordingly, preferred end products I are those in whose formulae $R^1$ is

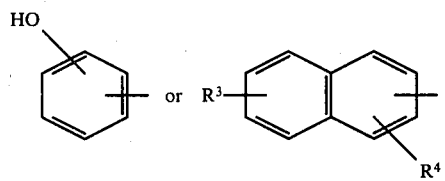

or alkyl of 1 to 18 carbon atoms, preferably 1 to 8 carbon atoms, which may be unsubstituted or may be polysubstituted or, preferably, monosubstituted, by alkoxy of 1 to 8 carbon atoms, alkoxyalkyleneoxy with alkyl of 1 to 4 carbon atoms and alkylene of 2 to 4 carbon atoms, dialkylamino of 1 to 4 carbon atoms per alkyl, aryloxy of 6 to 14 carbon atoms, especially of phenoxy, phenoxyethoxy and/or benzyloxy, or is cycloalkyl of 5 to 8 carbon atoms or aralkyl of 7 to 12 carbon atoms, $R^2$ is phenyl, which is unsubstituted or substituted by one or 2 alkyl each of 1 to 4 carbon atoms and/or one or 2 alkoxy each of 1 to 4 carbon atoms and/or one or 2 dialkylamino each of 1 to 4 carbon atoms per alkyl and/or one phenoxy, or is α-naphthyl or β-naphthyl which may be unsubstituted or substituted by one or 2 alkyl each of 1 to 4 carbon atoms and/or one or 2 alkoxy each of 1 to 4 carbon atoms and/or one or 2 dialkylamino each of 1 to 4 carbon atoms per alkyl and/or one phenoxy, and, if $R_1$ is

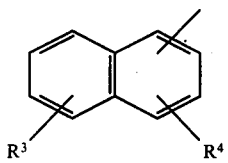

$R^2$ may be alkyl of 1 to 18 carbon atoms, and preferably 1 to 14 carbon atoms which may be unsubstituted or polysubstituted or, preferably, monosubstituted by alkoxy of 1 to 8 carbon atoms, alkoxyalkyleneoxy with alkyl of 1 to 4 carbon atoms and alkylene of 2 4 carbon atoms, dialkylamino of 1 to 8 carbon atoms per alkyl, phenoxy, phenoxyethoxy and/or benzyloxy, or may be cycloalkyl of 5 to 8 carbon atoms or aralkyl of 7 to 12 carbon atoms, $R^3$ and $R^4$ may be identical or different and each is hydrogen, alkyl of 1 to 8 carbon atoms, especially 1 to 4 carbon atoms, or alkoxy of 1 to 8 carbon atoms, especially 1 to 4 carbon atoms, and $R^5$ is hydrogen or, if $R^1$ is alkyl of 1 to 18 carbon atoms, preferably 1 to 8 carbon atoms, which may be unsubstituted, or polysubstituted or preferably monosubstituted by alkoxy of 1 to 8 carbon atoms, alkoxyalkyleneoxy with alkyl of 1 to 4 carbon atoms and alkylene of 2 to 4 carbon atoms, dialkylamino of 1 to 4 carbon atoms per alkyl or aryloxy each of 6 to 14 carbon atoms, especially phenoxy, phenoxyethoxy and/or benzyloxy, or is cycloalkyl of 5 to 8 carbon atoms or aralkyl of 7 to 12 carbon atoms, $R^5$ may also be alkyl of 1 to 18 carbon atoms, preferably 1 to 8 carbon atoms, which may be unsubstituted, or polysubstituted or preferably monosubstituted by alkoxy of 1 to 8 carbon atoms, alkoxyalkyleneoxy with alkyl of 1 to 4 carbon atoms and alkylene of 2 to 4 carbon atoms, dialkylamino of 1 to 4 carbon atoms per alkyl or aryloxy each of 6 to 14 carbon atoms, especially phenoxy, phenoxyethoxy and/or benzyloxy, or may be cycloalkyl of 5 to 8 carbon atoms or aralkyl of 7 to 12 carbon atoms. The above radicals may further be substituted by groups which are inert under the reaction conditions, e.g. alkyl or alkoxy of 1 to 4 carbon atoms.

The following are examples of suitable primary aromatic amine starting materials II: aniline which may be unsubstituted or substituted in the 2-, 3- or 4-position by methyl, ethyl, n-propyl, isopropyl, n-butyl, isobutyl or sec.-butyl, methoxyaniline, ethoxyaniline, n-propoxyaniline, isopropoxyaniline, n-butoxyaniline, isobutoxyaniline and sec.-butoxyaniline substituted in the o-, m- or p-position, aniline substituted in the 2-, 3- or 4-position by N,N-dimethylamino, N,N-diethylamino, N,N-di-n-propylamino, N,N-di-isopropylamino, N,N-di-n-butylamino, N,N-di-isobutylamino or N,N-di-sec.-butylamino, o-phenoxyaniline, m-phenoxyaniline and p-phenoxyaniline, aniline disubstituted in the 2,4-, 2,5-, 2,6-, 2,3-, 3,4- or 3,5-position by the above substituents, α-naphthylamine and β-naphthylamine.

Suitable secondary amines II are the above primary amines which in addition are substituted at the nitrogen atom by one of the following groups: methyl, ethyl, n-propyl, isopropyl, n-butyl, isobutyl, sec.-butyl, n-pentyl, n-hexyl, n-octyl, 2-ethyl-hexyl, 1,4-dimethylpentyl, cyclohexyl, cyclooctyl, benzyl, phenylethyl, phenylpropyl and phenylbutyl, ω-methoxy-, ω-ethoxy-, ω-n-propoxy-, ω-isopropoxy-, ω-n-butoxy-, ω-isobutoxy-, ω-sec.-butoxy-ethyl, ω-methoxy-, ω-ethoxy-, ω-n-propoxy-, ω-isopropoxy-, ω-n-butoxy-, ω-isobutoxyand ω-sec.-butoxy-propyl, ω-methoxybutyl, ω-ethoxybutyl, ω-n-propoxybutyl, ω-isopropoxybutyl, ω-n-butoxybutyl, ω-isobutoxybutyl and ω-sec.-butoxybutyl, ω-methoxy-, ω-ethoxy-, ω-n-propoxy-, ω-isopropoxy-, ω-n-butoxy-, ω-isobutoxy- and ω-sec.-butoxy-ethyleneoxyethyl and corresponding ethyleneoxypropyl and propyleneoxyethyl groups, phenoxy, benzyloxy ethyl, the groups —$(CH_2)_3OC_2H_4OCH_2C_6H_5$, —$(CH_2)_3OC_2H_4OC_2H_4C_6H_5$, —$(CH_2)_3OC_2H_4OC_6H_5$,

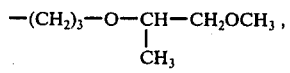

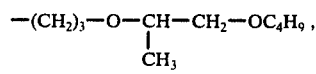

—$(CH_2)_3$—$OC_6H_5$, —$(CH_2)_3$—$OCH_2CH_2C_6H_5$, di-(methyl)-, di-(ethyl)-, di-(n-propyl)-, di-(isopropyl)-, di-(n-butyl)-, di-(isobutyl)- and di-(sec.-butyl)-amino-(ω)-propyl and corresponding ethyl, isopropyl, n-butyl, isobutyl, sec.-butyl, pentyl, pentyl-(2), pentyl-(3), n-hexyl and 3,3-dimethylbutyl-(1) groups which are substituted in the ω-position by the above dialkylamino groups,

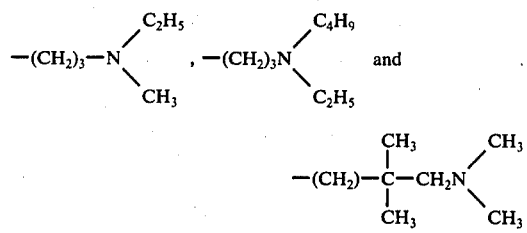

Appropriate mixtures of the above amines may also be used.

The following are examples of suitable primary aliphatic, cycloaliphatic and araliphatic amine starting materials II: methylamine, ethylamine, n-propylamine, isopropylamine, n-butylamine, isobutylamine, tert.-butylamine, sec.-butylamine, n-pentylamine, n-hexylamine, n-octylamine, 2-ethyl-hexylaime, 1,4-dimethyl-pentylamine, cyclohexylamine, cyclooctylamine, benzylamine, phenylethylamine, phenylpropylamine and phenylbutylamine, ω-methoxy-, ω-ethoxy-, ω-n-propoxy-, ω-isopropoxy-, ω-n-butoxy-, ω-isobutoxy-, ω-sec.-butoxy, ω-tert.butoxyethylamine, ω-methoxy-, ω-ethoxy-, ω-n-propoxy-, ω-isopropoxy-, ω-n-butoxy-, ω-isobutoxy-, ω-sec.-butoxy- and ω-tert.-butoxy-propylamine, ω-methoxybutylamine, ω-ethoxybutylamine, ω-n-propoxybutylamine, ω-isopropoxybutylamine, ω-n-butoxybutylamine, ω-isobutoxybutylamine, ω-sec.-butoxybutylamine and ω-tert.-butoxybutylamine, ω-methoxy-, ω-ethoxy-, ω-n-propoxy-, ω-isopropoxy-, ω-n-butoxy-, ω-isobutoxy-, ω-sec.-butoxy- and ω-tert.-butoxy-ethyleneoxy-ethylamine and corresponding ethyleneoxypropylamines and propyleneoxyethylamines, primary amines containing the radicals —$(CH_2)_3OC_2H_4OCH_2C_6H_5$, —$(CH_2)_3OC_2H_4OC_2H_4C_6H_5$, —$(CH_2)_3OC_2H_4OC_6H_5$,

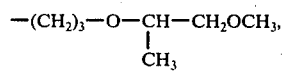

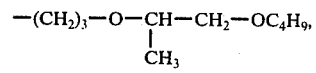

—$(CH_2)_3$—$OC_6H_5$ and
—$(CH_2)_3$—$OCH_2CH_2C_6H_5$, di-(methyl)-, di-(ethyl)-, di-(n-propyl), di-(isopropyl)-, di-(n-butyl)-, di-(isobutyl)- and di-(sec.-butyl)amino-(ω)-propylamines and corresponding ethylamines, isopropylamines, n-butylamines, isobutylamines, sec.-butylamines, tert.-butylamines, pentylamines, pentyl-(2)-amines, pentyl-(3)-amines, n-hexylamines and 3,3-dimethylbutyl-(1)-amines, which are substituted in the ω-position by the above dialkylamino groups, amines containing the radicals

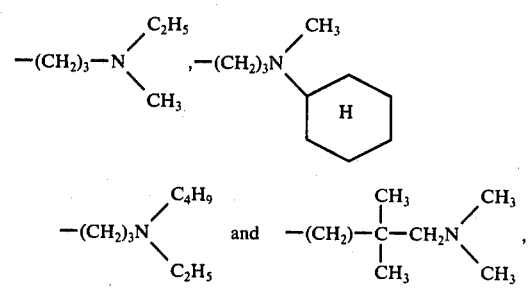

and appropriate mixtures of the above amines.

Suitable starting materials III are resorcinol, hydroquinone and, for example, the following naphthols: methyl-, ethyl-, n-propyl-, isopropyl-, n-butyl-, isobutyl- and sec.-butyl-α-naphthol and β-naphthol, the alkyl substituent being in the 3-, 4-, 5-, 6-, 7-, 8- or, respectively, the 2- or 1-position, preferably in the 2-, 4- or 5-position, corresponding methyl ethers, ethyl ethers, n-propyl ethers, isopropyl ethers, n-butyl ethers, isobutyl ethers and sec.-butyl ethers of the α- and β-naphthols which carry a further hydroxyl group in the above positions, α- and β-naphthol disubstituted in the 3,4-, 4,5-, 4,8-, 5,8- or 6,7-position by methyl, ethyl, n-propyl, isopropyl, n-butyl, isobutyl or sec.-butyl groups, corresponding trihydroxynaphthalenes of which 2 hydroxyl groups are etherified in the stated positions by the above alkyl groups, and corresponding α- and β-naphthols containing 2 different radicals from amongst those mentioned above, e.g. 4-ethyl-8-ethoxy-2-naphthol and 4-methyl-5-methoxy-naphthol; however, α- and β-naphthol are preferred.

The following are examples of suitable aliphatic, cycloaliphatic or araliphatic alcohol starting materials III: methyl, ethyl, n-propyl, isopropyl, n-butyl, isobutyl, sec.-butyl, n-pentyl, n-hexyl, n-octyl, 2-ethylhexyl and 1,4-dimethylpentyl alcohol, cyclohexyl, cyclooctyl, benzyl, phenylethyl, phenylpropyl and phenylbutyl alcohol, ω-methoxy-, ω-ethoxy-, ω-n-propoxy-, ω-isopropoxy-, ω-n-butoxy-, ω-isobutoxy- and ω-sec.-butoxy-ethyl alcohol, ω-methoxy-, ω-ethoxy-, ω-n-propoxy-, ω-isopropoxy-, ω-n-butoxy-, ω-isobutoxy- and ω-sec.-butoxy-propyl alcohol, ω-methoxybutyl, ω-ethoxybutyl, ω-n-propoxybutyl, ω-isopropoxybutyl, ω-n-butoxybutyl, ω-isobutoxybutyl and ω-sec.-butoxybutyl alcohol, ω-methoxy-, ω-ethoxy-, ω-n-propoxy-, ω-isopropoxy-, ω-n-butoxy-, ω-isobutoxy- and ω-sec.-butoxy-ethyleneoxy-ethyl alcohol and corresponding ω-alkoxyethyleneoxy-propyl alcohols and ω-alkoxypropyleneoxy-ethyl alcohols, alcohols which contain the groups —(CH$_2$)$_3$OC$_2$H$_4$OCH$_2$C$_6$H$_5$, —(CH$_2$)$_3$OC$_2$H$_4$OC$_2$H$_4$C$_6$H$_5$, —(CH$_2$)$_3$OC$_2$H$_4$OC$_6$H$_5$,

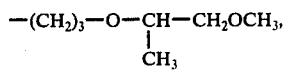

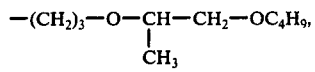

—(CH$_2$)$_3$—OCH$_2$CH$_2$C$_6$H$_5$ and —(CH$_2$)$_3$—OC$_6$H$_5$, di-(methyl)-, di-(ethyl)-, di-(n-propyl)-, di-(isopropyl)-, di-(n-butyl)-, di-(isobutyl)- and di-(sec.-butyl)-amino-(ω)-propyl alcohols and corresponding ethyl alcohols, isopropyl alcohols, n-butyl alcohols, isobutyl alcohols, sec.-butyl alcohols, pentyl alcohols, pentyl-(2) alcohols, pentyl-(3) alcohols, n-hexyl alcohols and 3,3-dimethyl-butyl-(1) alcohols substituted in the ω-position by such dialkylamino groups, alcohols where R$^4$ is

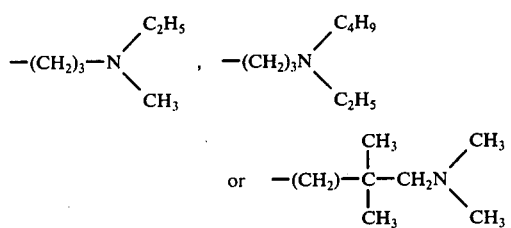

and approximate mixtures of the above alcohols.

The reaction is generally carried out at from 150° to 260° C, preferably from 175° to 235° C, especially from 200° to 230° C, under atmospheric or superatmospheric pressure, continuously or batchwise. Advantageously, it is carried out without added organic solvent; however, where appropriate, organic solvents which are inert under the reaction conditions and which preferably are immiscible or only slightly miscible with water, can be used; these are, advantageously, aromatic hydrocarbons, e.g. toluene, ethylbenzene, o-, m- and p-xylene, isopropylbenzene and methylnaphthalene, ethers, e.g. ethyl propyl ether, diisobutyl ether, methyl tert.-butyl ether, n-butyl ethyl ether, di-n-butyl ether, di-iso-amyl ether, diisopropyl ether, anisole, phenetole, cyclohexyl methyl ether and diethyl ether, aliphatic or cycloaliphatic hydrocarbons, e.g. heptane, nonane, o-, m- and p-cymene, gasoline fractions having a boiling range of from 70° to 190° C, cyclohexane, methylcyclohexane, decalin, hexane, petroleum ether, 2,2,4-trimethylpentane, 2,2,3-trimethylpentane, 2,3,3-trimethylpentane and octane, and appropriate mixtures. The solvent is advantageously used in an amount of from 400 to 10,000 percent by weight, preferably from 500 to 3,000 percent by weight, based on starting material II.

Advantageously, the catalyst is used in an amount of from 0.001 to 0.5, preferably from 0.005 to 0.1, mole of phosphorus-III compound per mole of starting material III. Preferred catalysts IV are those in whose formulae the individual R$^6$ radicals are identical or different and each is phenyl or naphthyl which may be unsubstituted or substituted by one or 2 alkyl each of 1 to 4 carbon atoms and/or one or 2 alkoxy each of 1 to 4 carbon atoms, or is hydrogen, alkyl of 1 to 7 carbon atoms or aralkyl of 7 to 12 carbon atoms. Examples of suitable catalysts are: tri-(2,6-dimethyl)-phenyl phosphite and tri(2-methoxy)-phenyl phosphite or preferably tri-o-tolyl phosphite, tri-m-tolyl phosphite and tri-p-tolyl phosphite, tri-o-xylyl phosphites, tri-m-xylyl phosphites and tri-p-xylyl phosphites, the ester group advantageously being in the m-position relative to one of the two methyl groups, tri-α-naphthyl phosphite, tri-β-naphthyl phosphite and especially triphenyl phosphite, trimethyl phosphite, triethyl phosphite, tri-(n-propyl) phosphite, tri-(iso-propyl) phosphite, tri(n-butyl) phosphite, tri-(iso-butyl) phosphite, tri-(sec.-butyl) phosphite, tri-(n-pentyl) phosphite, tri-(n-heptyl) phosphite, trioctyl phosphite, tri-(n-hexyl) phosphite, tristearyl phosphite and tridodecyl phosphite, dimethyl, diethyl, di-n-propyl, diisopropyl, di-n-butyl, diisobutyl, di-sec.-butyl, di-n-pentyl, di-n-heptyl, dioctyl, di-n-hexyl, distearyl and didodecyl phosphite, methyl phosphite, ethyl phosphite, propyl phosphite, isopropyl phosphite, butyl phosphite, isobutyl phosphite, sec.-butyl phosphite, n-pentyl phosphite, n-heptyl phosphite, octyl phosphite, n-hexyl phosphite, stearyl phosphite and dodecyl phosphite, phosphorous acid, tribenzyl phosphite, triphenylethyl phosphite, triphenylpropyl phosphite, dibenzyl phosphite, diphenylethyl phosphite, diphenylpropyl phosphite, benzyl phosphite, phenylethyl phosphite and phenylpropyl phosphite, di-(2,6-dimethyl)-phenyl phosphite, di-(2-methoxy)-phenyl phosphite, di-o-tolyl phosphite, di-m-tolyl phosphite and di-p-tolyl phosphite, di-o-xylyl phosphites, di-m-xylyl phosphites and di-p-xylyl phosphites, the ester groups advantageously being in the m-position relative to one of the two methyl groups, di-α-naphthyl phosphite, di-β-naphthyl phosphite and diphenyl phosphite, 2,6-dimethylphenyl phosphite, 2-methoxyphenyl phosphite, o-tolyl phosphite, m-tolyl phosphite, p-tolyl phosphite, o-xylyl phosphites, m-xylyl phosphites and p-xylyl phosphites, the ester group advantageously being in the m-position relative to one of the two methyl groups, α-naphthyl phosphite, β-naphthyl phosphite and phenyl phosphite, and corresponding phosphites with 3 of the above radicals of which, however, all or some are different from one another, e.g. phenyl dimethyl phosphite, methyl diethyl phosphite, methyl ethyl propyl phosphite, diphenyl butyl phosphite, phenyl diethyl phosphite, ethyl phenyl phosphite, butyl phenyl phosphite and benzyl diethyl phosphite.

The following are preferred: tri-n-butyl phosphite, tribenzyl phosphite, phosphorous acid, dibutyl phosphite, diisopropyl phosphite, dibenzyl phosphite, triisopropyl phosphite, distearyl phosphite, didodecyl phosphite, triphenyl phosphite, tritolyl phosphite, trixylyl phosphite, trinaphthyl phosphite, tri-n-hexyl phosphite, diphenyl phosphite, di-n-hexyl phosphite and benzyl diethyl phosphite.

The reaction can be carried out as follows: a mixture of catalyst IV, starting materials II and III, with or without solvent, is kept at the reaction temperature for from 1 to 30 hours, advantageously from 1 to 20 hours, in the case of the naphthylamines preferably from 4 to 20 hours and especially from 4 to 12 hours, and in the remaining cases for from 1 to 12 hours, advantageously from 1 to 8 hours and preferably from 2 to 4 hours. It is advantageous to heat the mixture at the reaction temperature until no more water distils off. The end product is then isolated from the mixture by conventional methods, e.g. by distillation. If the α- or β-naphthylamine produced is intended to be substantially free from the naphthol starting material, the oily crude naphthylamine phase is advantageously washed with dilute sodium hydroxide solution of from 1 to 10 percent strength by weight, to remove naphthol.

The arylamines I which can be manufactured by the process of the invention are valuable intermediates for the manufacture of crop protection agents, optical brighteners, especially aminocoumarin derivatives, and dyes, especially of the xanthene, pyronine, rhodamine, oxazine, azo, triphenylmethane and diphenylmethane series. Regarding their use, reference may be made to the cited publications, Ullmanns Encyklopadie der technischen Chemie, volume 12, pages 623 – 633 and vomume 17, pages 674 – 680, Kirk-Othmer, Encyclopedia of Chemical Technology, volume 2, pages 213 – 224 (1963) and volume 20, pages 701 – 732 (1969) and Venkataraman, The Chemistry of Synthetic Dyes, volume II (Academic Press, N.Y. 1952), pages 1074, 1094 and 1097.

In the Examples which follow, the parts are by weight.

EXAMPLE 1

3-Hydroxy-diphenylamine 250 parts of resorcinol, 250 parts of aniline and 4 parts of triphenyl phosphite are mixed. On heating to 120° C, a homogeneous melt is formed. When the internal temperature has reached 195° C, after 60 minutes, the elimination of water commences. The internal temperature is raised to a maximum of 235° C in the course of three hours. After this time, 41 parts of water have distilled off and the reaction has ended. Excess aniline and resorcinol which may still be present are removed under reduced pressure and the 3-hydroxy-diphenylamine is distilled at 215° C/12 mm Hg. 402 parts of 3-hydroxy-diphenylamine of melting point 76° – 79° C are obtained, corresponding to a yield of 96% of theory.

EXAMPLE 2

3-Hydroxy-4'-methyl-diphenylamine 250 parts of resorcinol, 268 parts of p-toluidine and 8 parts of triphenyl phosphite are mixed. A homogeneous melt is formed by heating to 120° C. When the internal temperature has reached 205° C, the elimination of water commences. The internal temperature is raised to 235° C in the course of 4 hours. After this time, no further water condenses in the water separator. In total, 41 parts of water are distilled off. Any excess aniline and resorcinol are distilled off under reduced pressure and the 3-hydroxy-4'-methyl-diphenylamine is then distilled, passing over at 185° C/2 mm Hg. 420 parts of 3-hydroxy-4'-methyl-diphenylamine of melting point 86° – 90° C obtained, corresponding to a yield of 93% of theory.

EXAMPLE 3

4-Hydroxy-diphenylamine 250 parts of hydroquinone, 220 parts of aniline and 10 parts of triphenyl phosphite are mixed and converted to a homogeneous melt by heating to 180° C. The elimination of water commences at an internal temperature of 198° C and has ended after 5 hours at 235° C. In total, 41 parts of water are removed. After distilling off excess aniline and hydroquinone, 4-hydroxy-diphenylamine is distilled off, passing over at 215° C/12 mm Hg. 382 parts of 4-hydroxy-diphenylamine of melting point 66° – 68° C are obtained, corresponding to a yield of 91% of theory.

EXAMPLE 4

3-Hydroxy-2'-methyl-diphenylamine 700 parts of resorcinol, 700 parts of o-toluidine and 15 parts of triphenyl phosphite are mixed. On heating to 120° C, a melt is formed. When the internal temperature has reached 205° C, the elimination of water commences. The internal temperature is raised to 230° C in the course of 4 hours. After this time, 115 parts of water have distilled off and the reaction has ended. Any excess aniline and resorcinol are removed by applying reduced pressure, and the 3-hydroxy-2'-methyl-diphenylamine is then distilled, passing over at 185° C/3 mm Hg. 1,190 parts of end product of $n_D^{25} = 1.6455$, corresponding to a yield of 94% of theory, are obtained.

EXAMPLE 5

3-Hydroxy-4'-methoxy-diphenylamine

Using the method described in Example 1, 220 parts of resorcinol, 300 parts of p-anisidine and 5 parts of triphenyl phosphite give 385 parts (90% of theory) of 3-hydroxy-4'-methoxy-diphenylamine of melting point 62° – 66° C.

EXAMPLE 6

3-Hydroxy-N-naphthyl-aniline

Using the method described in Example 1, 220 parts of resorcinol, 286 parts of α-naphthylamine and 8 parts of triphenyl phosphite give 411 parts (86% of theory) of 3-hydroxy-N-naphthyl-aniline, of boiling point 225° – 227° C/2 mm Hg.

EXAMPLE 7

N-phenyl-α-naphthylamine 144 parts of α-naphthol, 150 parts of aniline and 5 parts of triphenylphosphite are mixed and first heated to 180° C. The reaction commences, with elimination of water. The water is removed by means of a water separator and the aniline evolved is returned. The temperature rises to 210° in the course of 4 hours. After a further 4 hours at 212° C, the elimination of water has ended (18 parts of $H_2O$). The reaction mixture is cooled to 150° C and the excess aniline is distilled off under reduced pressure. Thereafter, 208 parts of phenyl-α-naphthylamine distil at 202° – 203° C/5 mm Hg; this product has a melting point of 55° – 58° C and corresponds to a yield of 95% of theory.

EXAMPLE 8

N-3-methylphenyl-α-naphthylamine 216 parts of α-naphthol, 214 parts of m-toluidine and 10 parts of triphenyl phosphite are mixed. The reaction is carried out analogously to Example 7. After removing 27 parts of water, the reaction has ended. After distilling off excess m-toluidine, 330 parts of N-m-tolyl-α-naphthylamine, corresponding to a yield of 94% of theory, are obtained at a boiling point of 203° – 206° C/5 mm Hg.

EXAMPLE 9

N-2,4-dimethyl-phenyl-α-naphthylamine 216 parts of α-naphthol, 242 parts of 2,4-dimethylaniline and 10 parts of triphenyl phosphite are mixed and the reaction is carried out using the method described in Example 7. The maximum reaction temperature is 220

C. After removing 27 parts of water, the reaction (which has taken 8 hours) has ended. 355 parts of N-2,4-dimethylphenyl-α-naphthylamine, of melting point 52° - 54° C, are obtained at a boiling point of 215° - 218° C/5 mm Hg. The yield is 95% of theory.

EXAMPLE 10

N-3,5-dimethyl-phenyl-α-naphthylamine

The reaction of 216 parts of α-naphthol with 242 parts of 3,5-dimethylaniline in the presence of 10 parts of triphenyl phosphite is carried out using the method described in Example 9. 350 parts of N-3,5-dimethyl-phenyl-α-naphthylamine of boiling point 215° - 216° C/5 mm Hg, are obtained, corresponding to a yield of 94% of theory.

EXAMPLE 11

N-p-ethoxy-phenyl-α-naphthylamine 288 parts of α-naphthol, 411 parts of p-phenetidine and 10 parts of triphenyl phosphite are mixed and heated to 220° C. At this temperature, the elimination of water commences. In the course of 8 hours, the reaction temperature rises to 250° C, at which stage the reaction has ended. 36 parts of water are removed. After removing excess p-phenetidine, N-p-ethoxy-phenyl-α-naphthylamine distils at a boiling point of 233° - 235° C/5 mm Hg. 510 parts of end product of melting point 73° - 75° C are obtained. This corresponds to a yield of 97% of theory.

EXAMPLE 12

1,1'-Dinaphthylamine 144 parts of α-naphthol, 143 parts of α-naphthylamine and 15 parts of triphenyl phosphite are mixed and heated to 220° C. The elimination of water commences at this temperature and has ended when the internal temperature reaches 250° C. 18 parts of water are removed in the course of 10 hours. After distilling off excess α-naphthol and α-naphthylamine, 250 parts of 1,1'-dinaphthylamine, of melting point 97° - 102° C, are obtained at 256° - 257°/5 mm Hg. This corresponds to a yield of 93% of theory.

EXAMPLE 13

N-phenyl-β-naphthylamine 270 parts of β-naphthol, 175 parts of aniline and 5 parts of triphenyl phosphite are mixed and fused at 130° C. The reaction commences at an internal temperature of 190° C, with elimination of water. After 2 ½ hours, internal temperature has reached 235° C and 34 parts of water have distilled off. 398 parts of N-phenyl-β-naphthylamine of melting point 100° - 102° are distilled, passing over at 230° C/15 mm Hg. This corresponds to a yield of 97% of theory.

EXAMPLE 14

1,2'-Dinaphthylamine 144 parts of β-naphthol, 143 parts of α-naphthylamine and 10 parts of triphenyl phosphite are mixed. A homogeneous melt is formed at 120° C internal temperature. The elimination of water commences when the internal temperature reaches 230° C and has ended after 3 hours, at an internal temperature of 250° C. 18 parts of water have distilled off. 258 parts of 1,2'-dinaphthylamine, of melting point 106° - 108° C, are obtained by distillation at 239° C/0.1 mm Hg. This corresponds to a yield of 96% of theory.

EXAMPLE 15

3-Hydroxy-diphenylamine

Using the method described in Example 1, 150 parts of resorcinol, 250 parts of aniline and 6 parts of tri-p-tolyl phosphite give 380 parts (90% of theory) of 3-hydroxy-diphenylamine of melting point 75° - 79° C.

EXAMPLE 16

3-Hydroxy-diphenylamine

Using the method described in Example 1, 250 parts of resorcinol, 250 parts of aniline and 10 parts of tri-3,4-dimethylphenyl phosphite give 382 parts (91% of theory) of 3-hydroxy-diphenylamine of melting point 74° - 78° C.

EXAMPLE 17

N-phenyl-α-naphthylamine 288 parts of α-naphthol, 205 parts of aniline and 10 parts of tributyl phosphite are mixed and first heated to 196° C. The reaction commences, with elimination of water. The water is removed by means of a water separator and the aniline which has escaped is returned. The internal temperature is raised to 235° C in the course of 8 hours. At this point, the elimination of water has ended (33 parts of water). The reaction mixture is cooled to 150° C and the excess aniline and α-naphthol are distilled off under reduced pressure. Thereafter, 400 parts of phenyl-α-naphthylamine are obtained at a boiling point of 202° - 203° C/5 mm Hg; the product has a melting point of 55° - 58° C and corresponds to a yield of 91% of theory.

EXAMPLE 18

N-3-methylphenyl-α-naphthylamine 216 parts of α-naphthol, 214 parts of m-toluidine and 10 parts of tributyl phosphite are mixed. The reaction is carried out using the method described in Example 17. After removing 24 parts of water, the reaction has ended. After distilling off excess m-toluidine 309 parts of N-m-tolyl-α-naphthylamine, corresponding to a yield of 88% of theory, are obtained at a boiling point of 203° - 206° C/5 mm Hg.

EXAMPLE 19

N-phenyl-α-naphthylamine 288 parts of α-naphthol, 205 parts of aniline and 10 parts of diphenyl phosphite are mixed and heated to 197° C. The elimination of water commences at this temperature and has ended when the internal temperature is 235° C. 31 parts of water are removed in the course of 8 hours. After distilling off excess α-naphthol and aniline, 372 parts of phenyl-α-naphthylamine are obtained at a boiling point of 202° - 204° C/5 mm Hg; the product has a melting point of 55° - 58° C and corresponds to a yield of 85% of theory.

EXAMPLE 20

N-phenyl-α-naphthylamine 288 parts of α-naphthol, 205 parts of aniline and 10 parts of diethyl phosphite are mixed and heated to 196° C. The elimination of water commences at this temperature and has ended when the internal temperature is 234° C. 27 parts of water are removed in the course of 8 hours. After distilling off excess α-naphthol and aniline, 330 parts of phenyl-α-naphthylamine are obtained at a boiling point of 203° – 205° C/5 mm Hg; the product has a melting point of 54° – 58° C and corresponds to a yield of 75% of theory.

EXAMPLE 21

3-Hydroxy-2'-methyldiphenylamine 250 parts of resorcinol, 300 parts of o-toluidine and 10 parts of tributyl phosphite are mixed. On heating to 120° C, a melt is formed. When the internal temperature has reached 190° C, the elimination of water commences. The internal temperature is raised to 230° C in the course of 5 hours. After this time, 41 parts of water have distilled off and the reaction has ended. Excess o-toluidine and resorcinol which may still be present are removed by applying reduced pressure, and the 3-hydroxy-2'-methyl-diphenylamine is then distilled, passing over at 185° C/3 mm Hg. 420 parts of end product of $N_D^{25} = 1.6455$ are obtained, corresponding to a yield of 93% of theory.

EXAMPLE 22

3-Hydroxy-2'-methyl-diphenylamine 250 parts of resorcinol, 300 parts of o-toluidine and 10 parts of diphenyl phosphite are mixed. On heating to 120° C, a melt is formed. When the internal temperature has reached 196° C, the elimination of water commences. The internal temperature is raised to 230 C in the course of 5 hours. After this time, 41 parts of water have distilled off and the reaction has ended. Excess o-toluidine and resorcinol which may still be present are removed by applying reduced pressure, and the 3-hydroxy-2'-methyl-diphenylamine is then distilled, passing over at 185° C/3 mm Hg. 416 parts of end product of $n_D^{25} = 1.6455$ are obtained, corresponding to a yield of 92% of theory.

EXAMPLE 23

3-Hydroxy-2'-methyl-diphenylamine 250 parts of resorcinol, 300 parts of o-toluidine and 10 parts of diethyl phosphite are mixed and heated to 193° C. The elimination of water commences at this temperature. The internal temperature is raised to 230° C in the course of 5 hours. After this time, 41 parts of water have distilled off and the reaction has ended. Excess o-toluidine and resorcinol which may be present are removed by applying reduced pressure and the 3-hydroxy-2'-methyl-diphenylamine is then distilled, passing over at 185° C/3 mm Hg. 407 parts of end product of $n_D^{25} = 1.6455$ are obtained, corresponding to a yield of 90% of theory.

EXAMPLE 24

N-phenyl-β-naphthylamine 288 parts of β-naphthol, 250 parts of aniline and 9 parts of tributyl phosphite are mixed and fused at 130° C. At 190° C internal temperature, the reaction commences, with elimination of water. After 5 hours, the internal temperature has reached 235° C and 34 parts of water have distilled off. Thereafter, 412 parts of N-phenyl-β-naphthylamine, of melting point 100° – 102° C, distil, passing over at 230° C/15 mm Hg. This corresponds to a yield of 94% of theory.

EXAMPLE 25

N-phenyl-β-naphthylamine 288 parts of β-naphthol, 220 parts of aniline and 6 parts of diphenyl phosphite are mixed and fused at 130° C. At 190° C internal temperature, the reaction commences, with elimination of water. After 5 hours, the internal temperature has reached 235° C and 36 parts of water have distilled off. Thereafter, 416 parts of N-phenyl-β-naphthylamine, of melting point 100° – 102° C, distil, passing over at 230° C/15 mm Hg. This corresponds to a yield of 95% of theory.

EXAMPLE 26

N-p-ethoxy-phenyl-α-naphthylamine 288 parts of α-naphthol, 411 parts of p-phenetidine and 8 parts of tribenzyl phosphite are mixed and heated to 218° C. At this temperature, the elimination of water commences. The reaction temperature rises to 250° C in the course of 10 hours. At that stage, the reaction has ended and 36 parts of water have been removed. After removing excess p-phenetidine, the N-p-ethoxy-phenyl-α-naphthylamine distils at a boiling point of 233° – 235° C/5 mm Hg. 479 parts of end product of melting point 72° – 75° C are obtained. This corresponds to a yield of 91% of theory.

EXAMPLE 27

N-phenyl-β-naphthylamine 288 parts of β-naphthol, 220 parts of aniline and 5 parts of phosphorous acid are mixed and heated to 173° C. At this temperature, the elimination of water commences. The reaction temperature rises to 230° C in the course of 4 hours. At that stage, the reaction has ended and 36 parts of water have been removed. The further working up is carried out as described in Example 8. 412 parts of N-phenyl-β-naphthylamine of melting point 100° – 102° C are obtained, corresponding to a yield of 94% of theory.

EXAMPLE 28

3-Hydroxy-2'-methyl-diphenylamine 250 parts of resorcinol, 300 parts of o-toluidine and 2.5 parts of phosphorous acid are mixed. At an internal temperature of 192° C, the elimination of water commences. The internal temperature is raised to 240° C in the course of 4 hours. After this time, 40 parts of water have distilled off and the reaction has ended. Excess o-toluidine and resorcinol which may be present are stripped off under reduced pressure and the 3-hydroxy-2'-methyl-diphenylamine is then distilled, passing over at 185° C/3 mm Hg. 407 parts of end product of $n_D^{25} = 1.6455$ are obtained, corresponding to a yield of 90% of theory.

EXAMPLE 29

N-phenyl-α-naphthylamine 288 parts of α-naphthol, 205 parts of aniline and 15 parts of benzyl diethyl phosphite are mixed and heated to 200° C. The elimination of water commences at this temperature and has ended when the internal temperature is 235° C. 33 parts of water are removed in the course of 5 hours. After distilling off excess α-naphthol and aniline, 381 parts of phenyl-α-naphthylamine, boiling at 202° – 204° C/5 mm Hg. are obtained; the product has a melting point of 55° – 58° C and corresponds to a yield of 87% of theory.

EXAMPLE 30

N-phenyl-α-naphthylamine 288 parts of α-naphthol, 205 parts of aniline and 10 parts of dibenzyl phosphite are mixed and heated to 195° C. The elimination of water commences at this temperature and has ended when the internal temperature is 235° C. 33 parts of water are removed in the course of 4 hours. After distilling off excess α-naphthol and aniline, 374 parts of phenyl-α-naphthylamine, boiling at 202° – 204° C/5 mm Hg, are obtained; the product has a melting point of 55° – 58° C and corresponds to a yield of 85% of theory.

EXAMPLE 31

N-methyl-β-naphthylamine 288 parts of β-naphthol, 3 parts of triphenyl phosphite and 80 parts of methylamine gas are heated for 10 hours under pressure at 200° C in a pressure autoclave. The pressure is 40 atmospheres. When the two-phase mixture has cooled, water is added, the batch is stirred for 30 minutes at 70° C and the lower oily phase is separated off and distilled. 305 parts of N-methyl-β-naphthylamine, boiling at 165° – 166° C/12 mm Hg, are obtained. This corresponds to a yield of 97% of theory.

EXAMPLE 32

N-ethyl-β-naphthylamine 288 parts of β-naphthol, 6.6 parts of triphenyl phosphite and 115 parts of ethylamine gas are heated for 10 hours at 230° C in a pressure autoclave. The pressure is 35 atmospheres. The mixture is added to 2,000 parts of water and the batch is stirred for 30 minutes at 70° – 80° C. The lower oily phase is separated off and distilled. 328 parts of N-ethyl-β-naphthylamine of boiling point 119° – 120° C/0.1 mm Hg are obtained. This corresponds to a yield of 96% of theory.

EXAMPLE 33

N-ethyl-α-naphthylamine 288 parts of α-naphthol, 10 parts of triphenyl phosphite and 100 parts of ethylamine gas are heated for 20 hours at 240° C, whilst stirring. After the mixture has cooled, it is next stirred for 20 minutes at 70° C with 1,000 parts of 2.5 percent strength by weight aqueous sodium hydroxide solution. The organic phase is separated off, washed with 2,000 parts of water at 30° C, again separated off and distilled. 308 parts of N-ethyl-α-naphthylamine boiling at 119° – 120° C/0.1 mm Hg are obtained, corresponding to a yield of 90% of theory.

EXAMPLE 34

N-butylamine-α-naphthylamine 288 parts of α-naphthol, 10 parts of triphenyl phosphite and 160 parts of n-butylamine are heated for 20 hours at 220° C in a pressure autoclave, whilst stirring. The further working up is carried out as described in Example 3. 346 parts of n-butyl-α-naphthylamine, boiling at 160° – 162° C/18 mm Hg, are obtained, corresponding to a yield of 87% of theory.

EXAMPLE 35

2-Methyl-N-ethyl-α-naphthylamine 316 parts of 2-methyl-α-naphthol, 10 parts of triphenyl phosphite and 115 parts of ethylamine gas are heated for 20 hours at 230° C in a pressure autoclave. The further working up is carried out as described in Example 3. 315 parts of 2-methyl-N-ethyl-α-naphthylamine, boiling at 120° – 125° C/0.3 mm Hg ($n_D^{25}$ = 1.6145) are obtained, corresponding to a yield of 85% of theory.

EXAMPLE 36

2-Phenylethyl-naphthylamine 288 parts of β-naphthol, 9 parts of triphenyl phosphite and 270 parts of 2-phenylethylamine are heated to 180° C whilst stirring. The elimination of water commences at this temperature and has ended after 5 hours at an internal temperature of 240° C. 36 parts of water are collected in the water separator. After distilling off excess β-naphthol and amine under reduced pressure, 2-phenylethyl-naphthylamine distils, at a boiling point of 230° – 231° C/5 mm Hg. 479 parts of 2-phenylethyl-naphthylamine are obtained, corresponding to a yield of 97% of theory.

EXAMPLE 37

2-[N-(2''-ethyl-hexoxy)-(3')-propyl]-naphthylamine 288 parts of β-naphthol, 9 parts of triphenyl phosphite and 410 parts of 3-(2'-ethylhexoxy)-propylamine are heated to 180° C whilst stirring. The elimination of water commences at this temperature and has ended after 8 hours, when the internal temperature is 230° C and 36 parts of water have been removed. Excess β-naphthol and amine are distilled off under reduced pressure and thereafter 2-[N-(2''-ethylhexoxy)-(3')-propyl]-naphthylamine are distilled at a boiling point of 220° – 221° C/3 mm Hg. 588 parts of end product are obtained, corresponding to a yield of 94% of theory.

EXAMPLE 38

2-Tridecyl-naphthylamine 288 parts of β-naphthol, 9 parts of triphenyl phosphite and 418 parts of tridecylamine are heated to 175° C, whilst stirring. The elimination of water commences at this temperature and has ended after 10 hours, when the internal temperature is 230° C and 36 parts of water have been removed. Excess β-naphthol and amine are distilled off in vacuo. 2-Tridecyl-naphthylamine is then distilled at a boiling point of 225° C/3 mm Hg. 630 parts of end product are obtained, corresponding to a yield of 97% of theory.

EXAMPLE 39

1-N-cyclohexyl-naphthylamine 144 parts of α-naphthol, 10 parts of triphenyl phosphite and 120 parts of cyclohexylamine are heated to 250° C in a stirred autoclave. After a reaction time of 20 hours, the autoclave is cooled and the pressure released. The excess α-naphthol and amine are distilled off under reduced pressure and thereafter 1-cyclohexyl-naphthylamine is distilled over a boiling point of 166° C/2 mm Hg. 191 parts of end product are obtained, corresponding to 85% of theory.

EXAMPLE 40

N-ethyl-α-naphthylamine 288 parts of α-naphthol, 10 parts of tributyl phosphite and 110 parts of ethylamine gas are heated for 20 hours at 240° C, whilst stirring. After cooling and letting down the autoclave, the mixture is stirred for 20 minutes with 1,000 parts of 2.5 percent strength by weight aqueous sodium hydroxide solution at 70° C. The organic phase is separated off, washed with 2,000 parts of water at 30° C, separated off and distilled. 290 parts of N-ethyl-α-naphthylamine boiling at 119° – 120° C/0.1 mm Hg are obtained, corresponding to a yield of 85% of theory.

EXAMPLE 41

N-ethyl-β-naphthylamine 288 parts of β-naphthol, 6 parts of diphenyl phosphite and 115 parts of ethylamine gas are heated at 230° C in a pressure autoclave for 10 hours. The pressure is 35 atmospheres. The mixture is added to 2,000 parts of water and the batch is stirred for 30 minutes at 70° – 80° C. The lower oily phase is separated off and distilled. 314 parts of N-ethyl-β-naphthylamine boiling at 119° – 120° C/0.1 mm Hg are obtained, corresponding to a yield of 92% of theory.

EXAMPLE 42

N-ethyl-β-naphthylamine 288 parts of β-naphthol, 5 parts of tribenzyl phosphite and 115 parts of ethylamine gas are heated at 230° C in a pressure autoclave for 10 hours. The pressure is 35 atmospheres. The mixture is added to 2,000 parts of water and the batch is stirred for 30 minutes at 70° – 80° C. The lower oily phase is separated off and distilled. 321 parts of N-ethyl-β-naphthylamine, boiling at 119° – 120° C/0.1 mm Hg are obtained, corresponding to a yield of 94% of theory.

EXAMPLE 43

1-N-cyclohexyl-naphthylamine 144 parts of α-naphthol, 6 parts of phosphorous acid and 120 parts of cyclohexylamine are heated to 250° C in a stirred autoclave. After a reaction time of 20 hours, the autoclave is cooled and let down. The excess α-naphthol and amine are distilled off in vacuo and the 1-cyclohexyl-naphthylamine is then distilled over at a boiling point of 166° C/2 mm Hg. 184 parts of end product are obtained, corresponding to 82% of theory.

EXAMPLE 44

2-[N-(2'-ethyl)-hexyl]-naphthylamine 288 parts of β-naphthol, 290 parts of 2-ethyl-hexylamine and 8 parts of triphenyl phosphite are heated to 160° C, whilst stirring. The elimination of water commences at this temperature and has ended after 5 hours, when the internal temperature is 210° C. 36 parts of water remain in the water separator. After distilling excess β-naphthol and amine under reduced pressure, the 2-[N-(2'-ethyl)-hexyl]-naphthylamine distils at a boiling point of 180° – 183° C/2 mm Hg. 485 parts of end product are obtained, corresponding to a yield of 95% of theory.

EXAMPLE 45

N-(2-phenylethyl)-m-toluidine 260 parts of phenylethyl alcohol, 428 parts of m-toluidine and 20 parts of triphenyl phosphite are mixed and heated, using a water separator, initially to 210° C, at which temperature the elimination of water commences. The internal temperature is raised to 236° C in the course of 8 hours. After this time, the elimination of water has ended (36 parts of water). After distilling off excess alcohol and amine, the N-(2-phenylethyl)-m-toluidine distils at a boiling point of 167° C/5 mm Hg. 402 parts of N-(2-phenylethyl)-m-toluidine (90% of theory) are obtained.

EXAMPLE 46

N-(2'-phenylethyl)-4-methoxy-aniline 244 parts of phenylethyl alcohol, 450 parts of p-anisidine and 30 parts of triphenyl phosphite are mixed and heated, using a water separator, initially to 210° C, at which temperature the elimination of water commences. The internal temperature is raised to 250° C in the course of 8 hours. After this time, the elimination of water has ended (36 parts of water). The mixture is worked up by distillation under reduced pressure. After distilling off excess alcohol and amine, the N-(2'-phenylethyl)-4-methoxy-aniline distils at a boiling point of 187° – 190° C/5 mm Hg. 372 parts of N-(2'-phenylethyl)-4-methoxyaniline (89% of theory) are obtained.

EXAMPLE 47

N-(2'-phenylethyl)-1-naphthylamine 122 parts of phenylethyl alcohol, 250 parts of α-naphthylamine and 10 parts of triphenyl phosphite are mixed and heated to 210° C. The elimination of water commences at this temperature. The mixture is heated to an internal temperature of 245° C in the course of 12 hours, after which the elimination of water has ended (33 parts of water). After removing excess amine and alcohol under reduced pressure, the N-(2'-phenylethyl)-1-naphthylamine distils at 225° – 230° C/5 mm Hg. 210 parts of N-(2'-phenylethyl)-1-naphthylamine (85% of theory) are obtained.

EXAMPLE 48

N-benzylaniline 200 parts of aniline, 108 parts of benzyl alcohol and 10 parts of triphenyl phosphite are heated for 20 hours at 240° C in a stirred autoclave. The autoclave is then let down and the water of reaction which has formed, the excess aniline and the unconverted alcohol are distilled off under reduced pressure. 165 parts of N-benzylaniline, corresponding to a yield of 90% of theory, distil at a boiling point of 125° C/0.2 mm Hg.

EXAMPLE 49

N-benzyl-4-methoxy-aniline 369 parts of p-anisidine, 162 parts of benzyl alcohol and 15 parts of triphenyl phosphite are first heated to 177° C. At this temperature, the elimination of water commences. The condensation has ended after 5 hours, when the internal temperature is 231° C. 27 parts of water are removed. Excess p-anisidine and excess benzyl alcohol are distilled off under reduced pressure. 265 parts of N-benzyl-4-methoxy-aniline, corresponding to a yield of 83% of theory, distil at 190° C/5 mm Hg.

EXAMPLE 50

N-(n-butyl)-m-toluidine 214 parts of m-toluidine, 75 parts of n-butanol and 10 parts of triphenyl phosphite are heated for 10 hours at 230° C in a stirred autoclave. The autoclave is then let down and the water of reaction formed, the excess of m-toluidine and the unconverted butanol are distilled off under reduced pressure. 130 parts of N-butyl-m-toluidine, corresponding to a yield of 80% of theory, distil at a boiling point of 65° – 70° C/0.2 mm Hg.

EXAMPLE 51

N-(β-diethylaminoethyl)-aniline 93 parts of aniline, 180 parts of 2-diethylaminoethanol and 10 parts of triphenyl phosphite are heated for 20 hours at 210° C in a stirred autoclave. The autoclave is then let down and the water of reaction formed, the excess aniline and the unconverted aminoalcohol are distilled under reduced pressure. 144 parts of N-(β-diethylaminoethyl)-aniline, corresponding to a yield of 75% of theory, distil at a boiling point of 185° – 187° C/15 mm Hg.

EXAMPLE 52

N,N-di-(2-phenylethyl)-m-toluidine 488 parts of phenylethyl alcohol, 214 parts of m-toluidine and 20 parts of triphenyl phosphite are heated, whilst stirring, to an internal temperature of 211° C. The elimination of water commences at this temperature and has ended after a reaction time of 15 hours, when the internal temperature is 242° C. Excess alcohol and unconverted amine are removed under reduced pressure. 410 parts of N,N-di-(2-phenylethyl)-m-toluidine, corresponding to a yield of 65% of theory, distil at a boiling point of 230° – 232° C/5 mm Hg.

EXAMPLE 53

N-(2-phenoxyethyl)-m-toluidine 138 parts of phenylglycol, 214 parts of m-toluidine and 15 parts of triphenyl phosphite are mixed whilst stirring and next heated to 210° C internal temperature. At this temperature, the elimination of water commences. The mixture is then heated to an internal temperature of 223° C in the course of 9 hours. During this time, 18 parts of water have distilled off and the condensation has ended. The excess starting material is then distilled off. 198 parts of N-(2-phenoxyethyl)-m-toluidine, corresponding to a yield of 87% of theory, distil at a boiling point of 186° – 192° C/5 mm Hg.

EXAMPLE 54

N-(2-butoxyethyl)-aniline 200 parts of aniline, 118 parts of butylgylcol and 10 parts of triphenyl phosphite are mixed whilst stirring and heated for 20 hours at 230° C in a stirred autoclave. The autoclave is then let down and the water of reaction formed, excess aniline and unconverted alcohol are distilled off. 143 parts of N-(2-butoxyethyl)-aniline, corresponding to a yield of 74% of theory, distil at a boiling point of 122° C/5 mm Hg.

EXAMPLE 55

N-ethyl-N-phenylethyl-aniline 182 parts of N-ethylaniline, 244 parts of phenylethyl alcohol and 20 parts of triphenyl phosphite are mixed whilst stirring and next heated to an internal temperature of 206° C, at which the elimination of water commences. The mixture is then heated to an internal temperature of 243° C in the course of 20 hours. During this time, 25 parts of water have distilled off and the condensation has ended. The excess ethylaniline and the unconverted alcohol are then distilled off. 274 parts of N-ethyl-N-phenylethyl-aniline, corresponding to a yield of 81% of theory, distil at a boiling point of 160° C/5 mm Hg.

EXAMPLE 56

N-ethyl-N-butyl-aniline 182 parts of N-ethylaniline, 150 parts of n-butanol and 10 parts of triphenyl phosphite are heated for 20 hours at 230° C in a stirred autoclave. The autoclave is then let down and the water of reaction formed, unconverted ethylaniline and excess alcohol are distilled off. 183 parts of N-ethyl-N-butyl-aniline, corresponding to a yield of 69% of theory, distil at a boiling point of 88° – 91° C/5 mm Hg.

EXAMPLE 57

N-cyclohexyl-m-toluidine 200 parts of cyclohexanol, 214 parts of m-toluidine and 10 parts of triphenyl phosphite are heated for 20 hours at 230° C in a stirred autoclave. The autoclave is then let down and the water of reaction formed, unconverted toluidine and excess alcohol are distilled off. 227 parts of N-cyclohexyl-m-toluidine, corresponding to a yield of 60% of theory, distil at a boiling point of 165° – 170° C/15 mm Hg.

EXAMPLE 58

N-ethylaniline 200 parts of aniline, 50 parts of ethyl alcohol and 10 parts of triphenyl phosphite are heated for 10 hours at 250° C in a stirred autoclave. The autoclave is then let down and the water of reaction formed, excess aniline and unconverted alcohol are distilled off under reduced pressure. 110 parts of N-ethylaniline, corresponding to a yield of 83% of theory, distil at a boiling point of 205° C/760 mm Hg.

EXAMPLE 59

N-ethyl-N-(2-N',N'-dimethylaminoethyl)-aniline 182 parts of N-ethylaniline, 150 parts of N,N-(dimethyl)-ethanolamine and 10 parts of triphenyl phosphite are heated for 20 hours at 230° C in a stirred autoclave. The autoclave is then let down and the water of reaction formed, unconverted ethylaniline and excess alcohol are distilled off under reduced pressure. 207 parts of N-ethyl-N-(2-N',N'-dimethylaminoethyl)-aniline, corresponding to a yield of 72% of theory, distil at a boiling point of 115° C/5 mm Hg.

EXAMPLE 60

N-ethyl-N-benzyl-aniline 182 parts of N-ethylaniline, 170 parts of benzyl alcohol and 10 parts of triphenyl phosphite are mixed whilst stirring and next heated to an internal temperature of 184° C, at which the elimination of water commences. The mixture is then heated to an internal temperature of 210° C in the course of 8 hours. During this time, 25 parts of water have distilled off and the condensation has ended. The excess ethylaniline and unconverted benzyl alcohol are then distilled off. 276 parts of N-ethyl-N-benzyl-aniline, corresponding to a yield of 87% of theory, distil at a boiling point of 140° – 144° C/5 mm Hg.

EXAMPLE 61

N-(2-phenoxyethyl)-m-toluidine 138 parts of phenylglycol, 214 parts of m-toluidine and 15 parts of diphenyl phosphite are mixed whilst stirring. The reaction is carried out using the method described in Example 9. 193 parts of N-(2-phenoxyethyl)-m-toluidine, corresponding to a yield of 85% of theory, are obtained at a boiling point of 186° – 192° C/5 mm Hg.

EXAMPLE 62

N-(2-phenoxyethyl)-m-toluidine 138 parts of phenylglycol, 214 parts of m-toluidine and 20 parts of tributyl phosphite are mixed whilst stirring and heated to an internal temperature of 210° C. The elimination of water commences at this temperature. The mixture is then heated to an internal temperature of 235° C in the course of 15 hours. During this time, 18 parts of water have distilled and the condensation has ended. 182 parts of N-(2-phenoxyethyl)-m-toluidine, corresponding to a yield of 80% of theory, distil at a boiling point of 186° – 192° C/5 mm Hg.

We claim:

1. A process for the manufacture of arylamines of the formula

   I where $R^1$ is

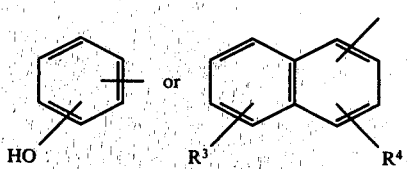

or is an aliphatic, cycloaliphatic or araliphatic radical, $R^2$ is an aromatic radical and, if $R^1$ is

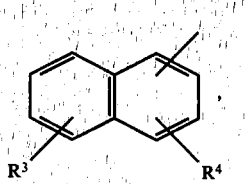

may also be an aliphatic, cycloaliphatic or araliphatic radical, $R^3$ and $R^4$ may be identical or different and each is hydrogen, an aliphatic radical or alkoxy and $R^5$ is hydrogen or, if $R^1$ is an aliphatic, cycloaliphatic or araliphatic radical, may also be an aliphatic, cycloaliphatic or araliphatic radical, wherein amines of the formula

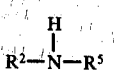   II where $R^2$ and $R^5$ have the above meanings, are reacted with alcohols of the formula

   III where $R^1$ has the above meanings, in the presence of a phosphorus-III compound of the formula

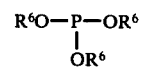   IV where the individual $R^6$ radicals may be identical or different and each is hydrogen or an aliphatic, araliphatic or aromatic radical, as the catalyst.

2. A process as claimed in claim 1, wherein primary aromatic amines of the formula

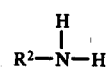   II where $R^2$ is an aromatic radical, are reacted with phenols of the formula

   III where $R^1$ is

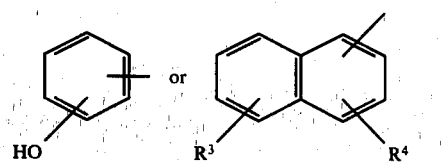

and $R^3$ and $R^4$ may be identical or different and each is hydrogen, an aliphatic radical or alkoxy, in the presence of a triaryl phosphite of the formula

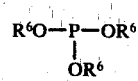   IV where the individual $R^6$ radicals may be identical or different and each is an aromatic radical, as the catalyst.

3. A process as claimed in claim 1, wherein primary aromatic amines of the formula

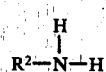   II where $R^2$ is an aromatic radical, are reacted with phenols of the formula

   III where $R^1$ is

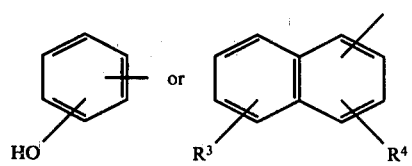

and $R^3$ and $R^4$ may be identical or different and each hydrogen, an aliphatic radical or alkoxy, in the presence of a phsophorus-III compound of the formula

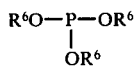

where the individual $R^6$ radicals may be identical or different and each is hydrogen or an aliphatic or araliphatic radical, and one or two $R^6$ radicals may also each be an aromatic radical, as the catalyst.

4. A process as claimed in claim 1, wherein primary amines of the formula

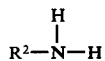

where $R^2$ is an aliphatic, cycloaliphatic or araliphatic radical, are reacted with naphthols of the formula

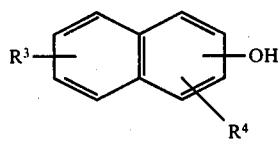

where $R^3$ and $R^4$ may be identical or different and each is hydrogen or an aliphatic radical or alkoxy, in the presence of a phosphorus-III compound of the formula

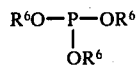

where the individual $R^6$ radicals may be identical or different and each is hydrogen or an aliphatic, araliphatic or aromatic radical, as the catalyst.

5. A process as claimed in claim 1, wherein aromatic amines of the formula

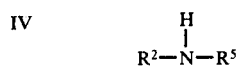

where $R^5$ is an aliphatic, cycloaliphatic or araliphatic radical or hydrogen and $R^2$ is an aromatic radical, are reacted with alcohols of the formula $$R^1 - OH \qquad \text{III}$$

where $R^1$ is an aliphatic, cycloaliphatic or araliphatic radical, in the presence of a phosphorus-III compound of the formula

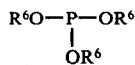

where the individual $R^6$ radicals may be identical or different and each is hydrogen or an aliphatic, araliphatic or aromatic radical, as the catalyst.

6. A process as claimed in claim 1, wherein the reaction is carried out with from 1 to 3.5 moles of starting material II per mole of alcohol III.

7. A process as claimed in claim 1, wherein the reaction is carried out with from 0.3 to 4 moles of starting material II per mole of alcohol III.

8. A process as claimed in claim 1, wherein the reaction is carried out at from 150° to 260° C.

9. A process as claimed in claim 1, wherein the reaction is carried out at from 175° to 235° C.

10. A process as claimed in claim 1, wherein the reaction is carried out at from 200° to 230° C.

11. A process as claimed in claim 1, wherein the reaction is carried out with from 0.001 to 0.5 mole of phosphorus-III compound per mole of starting material III.

12. A process as claimed in claim 1, wherein the reaction is carried out with from 0.005 to 0.1 mole of phosphorus-III compound per mole of starting material III.

* * * * *

UNITED STATES PATENT AND TRADEMARK OFFICE
CERTIFICATE OF CORRECTION

PATENT NO. : 4,067,903
DATED : January 10, 1978
INVENTOR(S) : Helmut Hoch and Horst Scheuermann It is certified that error appears in the above-identified patent and that said Letters Patent are hereby corrected as shown below:

Column 26, line 66, after "each" insert --is--.

Signed and Sealed this

Thirteenth Day of June 1978

[SEAL]

Attest:

RUTH C. MASON
Attesting Officer

DONALD W. BANNER
Commissioner of Patents and Trademarks